(12) United States Patent
Kraft

(10) Patent No.: US 9,227,023 B2
(45) Date of Patent: Jan. 5, 2016

(54) DEVICE FOR THE RAPID INJECTION OF LOCAL ANESTHESIA THROUGH A PLEURALITY OF NEEDLES

(71) Applicant: Joseph Wayne Kraft, College Station, TX (US)

(72) Inventor: Joseph Wayne Kraft, College Station, TX (US)

(*) Notice: Subject to any disclaimer, the term of this patent is extended or adjusted under 35 U.S.C. 154(b) by 220 days.

(21) Appl. No.: 14/010,430

(22) Filed: Aug. 26, 2013

(65) Prior Publication Data

US 2014/0200552 A1 Jul. 17, 2014

Related U.S. Application Data

(62) Division of application No. 13/744,344, filed on Jan. 17, 2013, now Pat. No. 8,632,501.

(51) Int. Cl.
| | |
|---|---|
| *A61M 5/00* | (2006.01) |
| *A61M 5/46* | (2006.01) |
| *A61M 5/32* | (2006.01) |
| *A61M 5/42* | (2006.01) |
| A61M 37/00 | (2006.01) |

(52) U.S. Cl.
CPC .............. *A61M 5/46* (2013.01); *A61M 5/3295* (2013.01); *A61M 5/422* (2013.01); *A61M 5/427* (2013.01); *A61M 2037/0023* (2013.01)

(58) Field of Classification Search
CPC ................ A61M 2037/0023; A61M 5/422
See application file for complete search history.

(56) References Cited

U.S. PATENT DOCUMENTS

| 2,817,336 | A | * | 12/1957 | Kravitz et al. | 604/47 |
|---|---|---|---|---|---|
| 5,250,023 | A | * | 10/1993 | Lee et al. | 604/20 |
| 8,088,108 | B2 | | 1/2012 | Kraft | |
| 8,409,147 | B2 | * | 4/2013 | Kraft | 604/173 |
| 8,419,708 | B2 | * | 4/2013 | Tokumoto et al. | 604/506 |
| 8,632,501 | B2 | * | 1/2014 | Kraft | 604/173 |
| 2011/0137250 | A1 | | 6/2011 | Kraft | |
| 2013/0231633 | A1 | * | 9/2013 | Kraft | 604/506 |
| 2014/0200552 | A1 | * | 7/2014 | Kraft | 604/512 |

* cited by examiner

*Primary Examiner* — Aarti B Berdichevsky
(74) *Attorney, Agent, or Firm* — Furr Law Firm; Jeffrey Furr, Esq.

(57) ABSTRACT

This device is a compressible chamber designed to inject a liquid medication through a plurality of needles. It is a self-contained, rapidly deployed device that replaces a classic syringe. It consists of a shallow chamber that is closed on one end and sealed on the other with a sliding elastomeric seal. A rigid ring slides up into the chamber that has multiple small double-ended needles mounted through the periphery of the ring perpendicularly so as to be able to perforate the seal of the chamber with the proximal end and simultaneously penetrate the subcutaneous tissues with the distal end thus allowing medication to flow from the chamber into the tissues when pressure is applied to the top of the chamber. The needles are also imbedded in, or juxtapose to a ring of compressible dye-containing material that serves to conceal the needles and provide demarcation of the area injected.

9 Claims, 5 Drawing Sheets

DEVICE FOR THE RAPID INJECTION OF LOCAL ANESTHESIA THROUGH A PLURALITY OF NEEDLES

CROSS-REFERENCES TO RELATED APPLICATIONS

This is the Non-provisional Divisional Application to application Ser. No. 13/744,344 filed Jan. 17, 2013.

STATEMENT AS TO RIGHTS TO INVENTIONS MADE UNDER FEDERALLY SPONSORED RESEARCH AND DEVELOPMENT

None

FIELD OF THE INVENTION

This device refers to the field of injection of an anesthetic into the subcutaneous tissues; more specifically it refers to the method of injecting medication subcutaneously in a manner that greatly reduces the pain and psychological anxiety of such injections.

BACKGROUND OF THE INVENTION

The injection of a local anesthetic is performed routinely in a clinical setting in order to provide anesthesia of the skin for painful procedures such as laceration repairs, biopsies, lumbar punctures, the introduction of intravenous (IV) catheters, the incision and drainage of abscesses and many more dermatologic procedures. Traditionally this was performed by the use of multiple subcutaneous injections with a hypodermic needle into the periphery of the area to be anesthetized. The invention of the Rapid Local Anesthesia Injection Cone, U.S. Pat. No. 8,088,108 incorporated by reference, greatly improved the speed with which this can be done while also greatly reducing the overall discomfort and anxiety. The Rapid Local Anesthesia Injection Cone, reviewed for clarity, utilizes a flat base with multiple very small gauge needles imbedded in the circumference and these needles are buried in or juxtaposed to a compressible ring of skin marking foam rubber or other similar compressible material, which then renders the needles effectively invisible. This allows for a very rapid injection of local anesthetic without the use of visible needles while also providing a well-demarcated ring of skin dye to indicate the exact area of anesthesia.

While the Injection Cone greatly improved this painful procedure, there are situations where this proposed device would add even more overall benefit. The previous device improves the procedure in many ways but it still has the overall appearance of being a hypodermic syringe and is being utilized and handled in much the same manner as such. This similarity will continue to cause significant fear and anxiety in many individuals. This proposed device would greatly improve the speed of injection while simultaneously decreasing significantly the pain and psychological trauma associated with local anesthesia. Although this device would be most commonly employed for administration of local anesthesia, it would serve well for shallow injection of any liquid medication.

This proposed device would have a base such as that described in the Rapid Local Anesthesia Injection Cone, U.S. Pat. No. 8,088,108 incorporated by reference, but in place of the cone with a syringe attached, there would be a self contained anesthetic chamber which contains a compressible bladder or broad based vial of anesthetic.

There remains room for improvement in the current device.

SUMMARY OF THE INVENTION

This proposed device is a compressible chamber intended to replace the cone and syringe parts of the Rapid Local Anesthesia Injection Cone, U.S. Pat. No. 8,088,108.

To establish points of reference, henceforth the "top" of the device will also be referred to as the "proximal end" of the device, which is the closed end of the chamber. The "bottom" of the device will also be referred to the "distal end" of the device, which is the end of the device that contains needles and compressible foam ring.

The chamber can be, but is not limited to a low profile cylindrical-shaped rigid structure that is open on the distal end where it is sealed by a moveable elastomeric seal. This seal would be free to be pushed in an axial direction proximally into the chamber by forces placed on it by the base ring, which has imbedded into it, traversing the ring perpendicularly in the axial direction, multiple needles, which are sharpened on both ends. When the base ring is forced into the chamber, the proximal ends of the needles perforate the elastomeric seal, thus allowing the liquid medication in the chamber to flow through the needles when the pressure in the chamber increases. When the distal end of the device is pressed against the skin, there is a subsequent axial force that pushes the base ring toward the proximal end of the chamber. This force causes the proximal ends of the needles to penetrate the elastomeric seal and the distal ends of the needles to penetrate into the tissues. As the force continues to slide the base ring proximally, the base ring forces the elastomeric seal toward the proximal end of the chamber thereby increasing the pressure inside the chamber and forcing the liquid medication to exit the chamber through the lumens of the needles and into the tissues to be medicated. The number of needles would be directly proportional to the circumference of the device. An alternative embodiment may include a pliable bladder type chamber as well. Lastly, there is a compressible ring that may be made of foam rubber or other similar compressible compound that is affixed to the distal end of the base ring and contains a skin marking dye. This compressible ring serves both to conceal the distal ends of the needles and to demarcate onto the skin the exact area that was injected. This is particularly helpful when the device is utilized for the purpose of local anesthesia thus demarcating the area of the skin that is anesthetized and preventing the inadvertent extension of a painful procedure out into the non-anesthetized tissues.

The device would be available in many sizes identified by the circumference of the base of the device. These sizes could be denoted in, but not limited to, 5 mm increments.

BRIEF DESCRIPTION OF DRAWINGS

Without restricting the full scope of this invention, the preferred form of this invention is illustrated in the following drawings in which.

DETAILED DESCRIPTION OF THE PREFERRED EMBODIMENT

Figure 1:
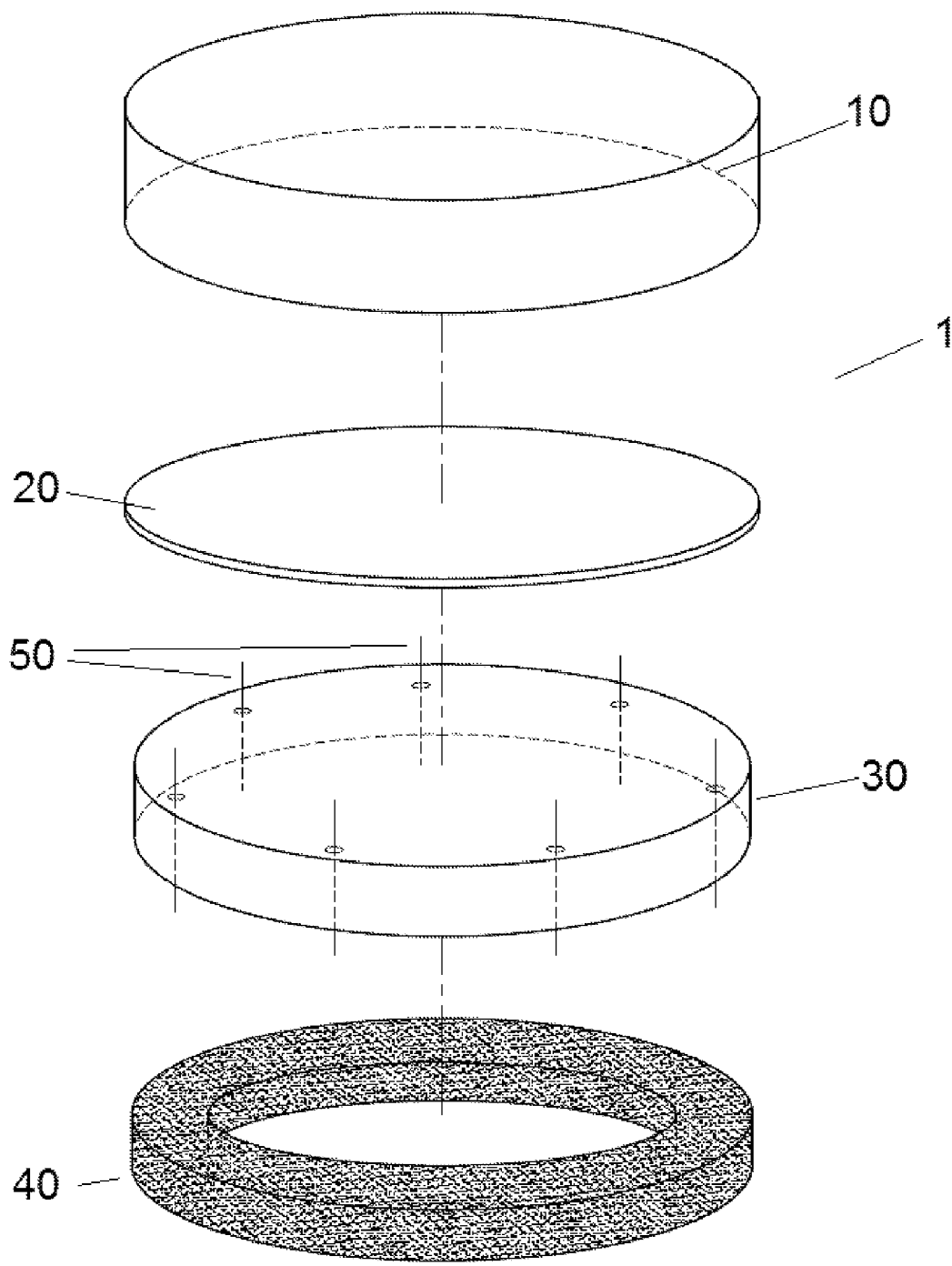
FIG. 1 is an exploded view of the device demonstrating the 4 basic units.

There are a number of significant design features and improvements incorporated within the invention.

The Rapid Local Anesthesia Injection Cone, U.S. Pat. No. 8,088,108, significantly improved the unpleasant experience of local anesthesia in many ways. The duration of the discomfort is now minimized to only 1-2 seconds. The psychological trauma is now limited greatly by there being no visible needle penetration. The area of anesthesia is now very well demarcated thus preventing inadvertent extension of painful procedures outside of the area of anesthesia. The total procedure time is now greatly reduced and the amount of user variability is greatly controlled thus producing much more uniform and consistent resultant anesthesia. As much as this device improved patient care, there remained room for improvement in some applications of this device. This proposed device is designed to make the Rapid Local Anesthesia Injection Cone (U.S. Pat. No. 8,088,108) even more versatile by making it more simple to use, compact and appear less like a traditional hypodermic syringe thus further reducing the psychological trauma associated with local anesthesia.

As shown in FIG. 1 through 6, this device is designed to be used in conjunction with the base assembly of the Rapid Local Anesthesia Injection Cone, U.S. Pat. No. 8,088,108 incorporated by reference, and to replace the use of a typical syringe. This device 1 is comprised of a chamber 10 to hold a liquid such as a liquid medication or anesthesia, a base structure 30 with perpendicular needles 50 which are sharp on both ends penetrating the base at 90 degrees and a dye impregnated ring of compressible material 40 which could be made of foam rubber or other similar compressible material and it may be but is not limited to being ring-shaped, and it will be referred to as a compressible ring 40 henceforth.

The chamber 10 can be, but is not limited to a low profile cylindrical shaped rigid structure that is open on the distal end where it can be sealed by a moveable elastomeric seal 20. The seal 20 would be free to be pushed up into the chamber 10 by forces placed on it by the base structure 30. The entire seal does not need to be elastomeric, as the center portion could be made of a rigid material in a different embodiment. The chamber 10 could also be constructed of an elastomeric collapsible material in other embodiments.

When pressure is placed on the top of the chamber 10 the elastomeric seal 20 will be pressed against the needles 50 allowing the point at the proximal end of the needles 50 to penetrate through the elastomeric seal 20 and force the liquid injectate 120 such as a liquid medication or anesthesia through the needles 50 which are protruding into, or juxtaposed to, the compressible ring 40. It is designed in such a way that when the compressible ring 40 is compressed against an area of skin 130 the needles 50 will penetrate through the skin 130 and into a space below the skin, henceforth referred to as the subcutaneous tissues 140, thus allowing the injectate 120 to be transferred from the chamber 10 to the subcutaneous tissues. With this design, the same force that forces the injectate 120 out of the chamber 10 also pushes the needles 50 through the skin 130.

FIG. 1 shows an exploded view of the device 1 demonstrating the four basic units. The anesthesia chamber 10 is cylindrical with a closed end and an open end in the preferred embodiment but could be other shapes as well. The elastomeric seal 20 fits into the anesthesia chamber to seal the liquid injectate 120 such as a liquid medication or anesthesia into the chamber 10 and thus maintain sterility. The chamber 10 fits over the base structure 30 so that the base structure 30 can slide up inside the walls of the anesthesia chamber 10. Ideally, the chamber 10 and base structure would be fashioned in such a way to have mating surfaces that would require a partial rotation or other maneuver in order to "arm" the device and render it ready for use.

The base structure 30 has needles 50 that are beveled on both ends distributed around the outside of the base structure 30 and protruding through the base structure perpendicularly in an axial direction. The base structure 30 serves to hold the needles 50 in position as well as to act as a plunger to force the liquid injectate 120 out of the chamber 10. As the pressure is placed on the top of the chamber 10, it forces the base structure 30 up inside of the chamber 10 forcing the needles 50 to penetrate the elastomeric seal 20 and force the seal 20 up into the chamber 10 thus displacing the liquid injectate 120 through the needles 50, through the skin 130 and into the subcutaneous tissues 140.

The compressible ring 40 attached to the base structure 30 is impregnated with skin-marking dye 70. This compressible ring 40 is ring-shaped in this depiction, but may be other shapes as well as determined by the footprint of the device. This compressible ring 40 serves to hide the distal ends of the needles 50 until it is compressed when pushed against the skin 130. This can be accomplished by either having the needles 50 imbedded in the compressible ring 40 or juxtaposed to the inner aspect of the compressible ring 40. The length of the needles 50 will be determined by the compressibility of the material used in the compressible ring 40. Ideally when the compressible ring 40 is compressed, the needles 50 would have a reveal of approximately, but not limited to, 3 mm to allow the needles to penetrate the skin 130 and enter the subcutaneous tissues 140. The compressible ring 40 would simultaneously mark the skin 130 with the skin marking dye 70, thus clearly demarcating the area of subcutaneous tissue 140 that has been infiltrated with medication 120.

Figure 2:
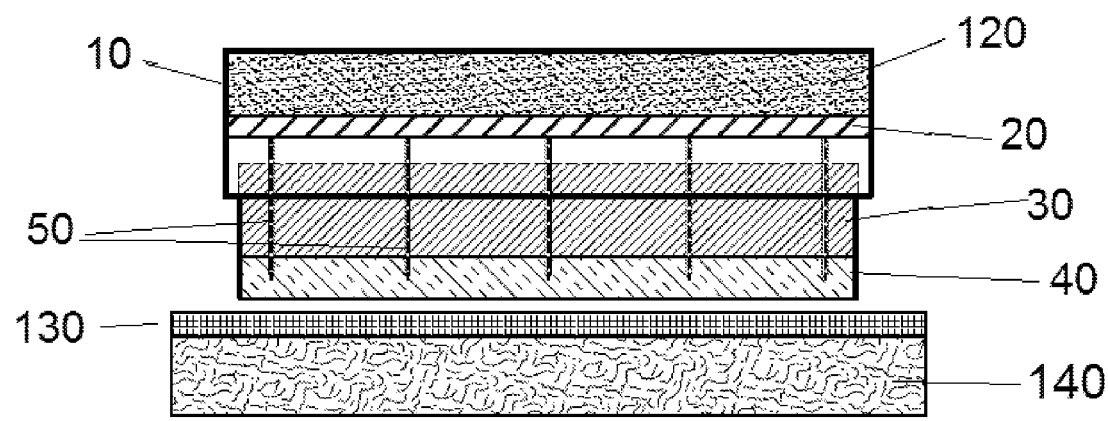
FIG. 2 is a side view of the device in its ready state (pre-injection)

FIG. 2 is a side view of the device 1 in its ready state (pre-injection). In this view the needles 50 have not yet penetrated the elastomeric seal 20 and thus the liquid injectate 120 is still sealed in a sterile manner within the chamber 10. Also note that the distal ends of the needles 50 are still embedded in or juxtaposed to the compressible ring 40 with no part of them being visible. This is the state in which the device 1 would be when laid upon the skin 130 prior to having any forced applied.

Figure 3:
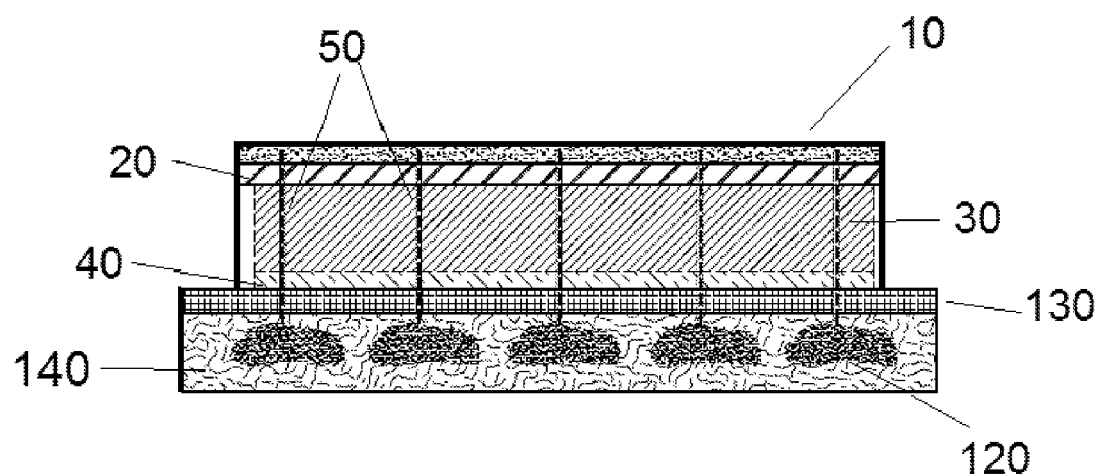
FIG. 3 is a side view of the device in the spent state (post-injection)

FIG. 3 displays a side view of the device 1 in the spent state (post-injection). In this view the chamber 10 has already been forced down against the skin 130 which simultaneously forced the base structure 30 proximally and thus forced the needles 50 to penetrate the elastomeric seal 20 with the proximal ends while simultaneously penetrating the skin 130 with the distal ends and allowed the injectate 120 to travel from the chamber 10 through the needles 50 and into the subcutaneous tissues 140. Note that in this post-injection state, the liquid injectate 120 has been diffusely infiltrated into the subcutaneous tissues thus creating optimum infiltration of the nerves that innervate the overlying skin. This is particularly important when used for local anesthesia.

Figure 4:
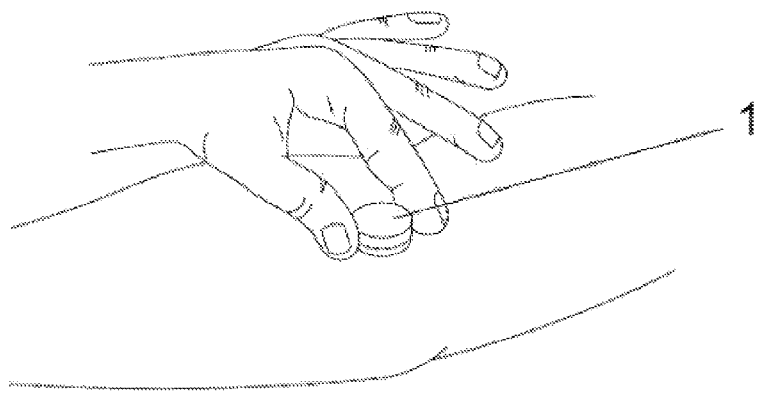
FIG. 4 depicts the device being placed on the skin of a forearm to anesthetize the skin over the antecubital veins prior to IV catheter placement.

FIG. 4 shows the device 1 being placed on the skin 130 of a forearm to anesthetize the skin over the antecubital veins prior to intravenous catheter placement.

Figure 5:
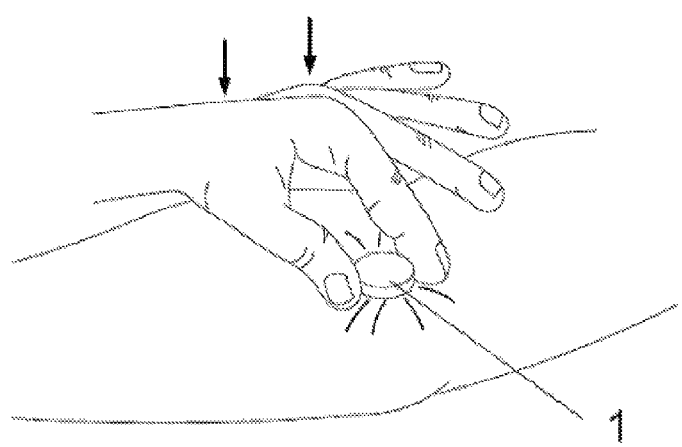
FIG. 5 depicts the device being pressed down against the skin forcing the foam ring to compress and pushing the needles through the skin and subsequently injecting the medication into the subcutaneous tissues.

FIG. 5 shows the device 1 being pressed down against the skin 130 at the injection site forcing the compressible ring 40 to compress and pushing the needles 50 into the subcutaneous tissues 140. The same force simultaneously expels the liquid injectate 120 into the subcutaneous tissues 140.

Figure 6:
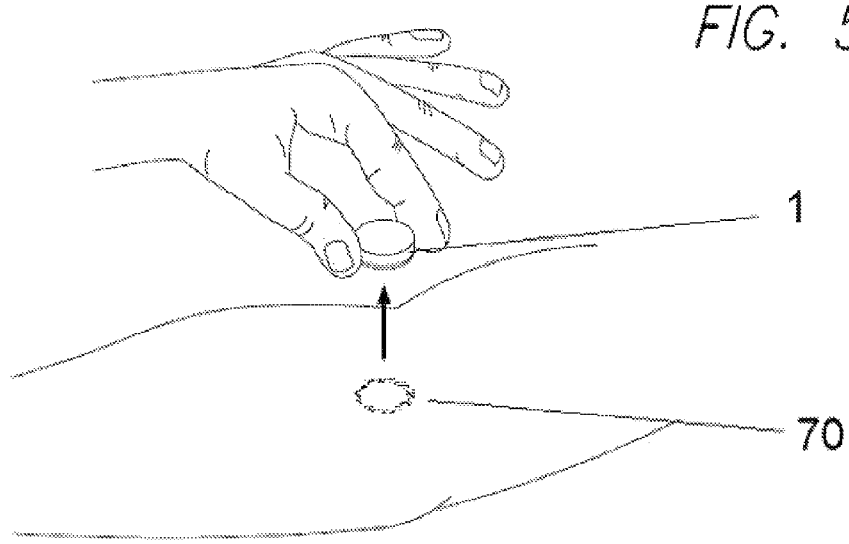
FIG. 6 depicts the forearm after injection of anesthesia demonstrating a well-demarcated area of anesthesia.

FIG. 6 shows the injection site, which in this case is the forearm, after injection of injectate 120 demonstrating a well-demarcated area of anesthetic infiltration thus allowing for a painless insertion of the intravenous catheter.

As shown in FIG. 2, protruding from the base 30 are multiple tiny hypodermic needles 50. The number of needles 50 would be directly proportional to the circumference of the base 30 of the device 1 and spaced in such a manner as to allow for complete infiltration of the subcutaneous tissues 140.

The device 1 can be made in many sizes identified by the shape and the length of the base 30 of the device 1. These sizes could be denoted in, but not limited to, 5 mm increments. This would allow for significant individualization of the device determined by the size and shape of the area that needs to be anesthetized.

The needles 50 protrude from the base structure 30 approximately 3-5 mm in the preferred embodiment and the distal ends are buried in a compressible material 40 which is adherent to the base of the device 1. This material could be, but is not limited to being made of foam rubber or other similar material. The length of the needles 50 is dependent on the compressibility factor of this material 40.

The demarcating the area of infiltration as shown in FIG. 6 is used to identify exactly where the injectate 120 has been applied and could be color-coded or pattern-coded to identify the type of medication used. This color-coding would allow health professionals to make sure that a patient is properly dosed.

Although local anesthetic would be the most common use of this device, it can certainly be used for the injection of other liquids and liquid medications as well.

Figure 7:
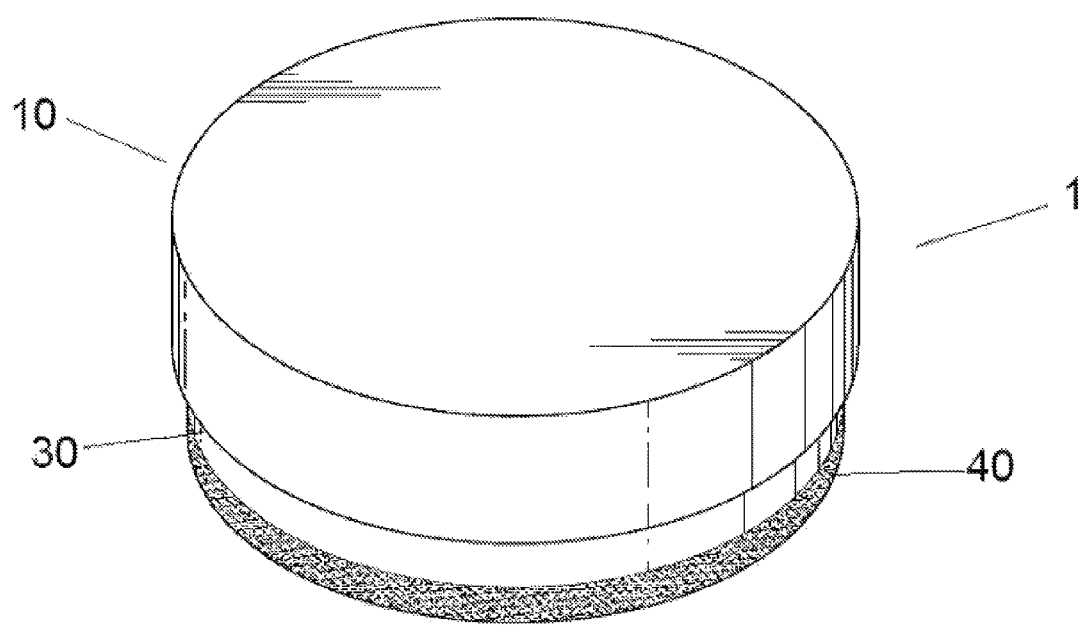
FIG. 7 is a prospective side view of the device in its ready state (pre-injection)
Figure 8:
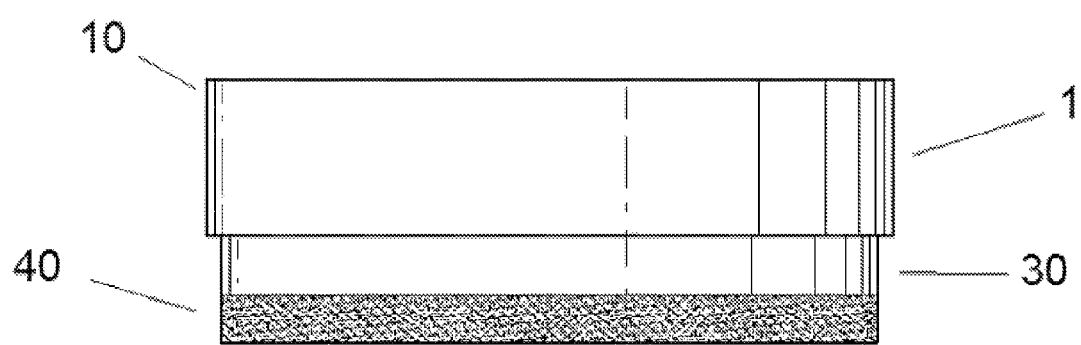
FIG. 8 is a side view of the device (pre-injection)
Figure 9:
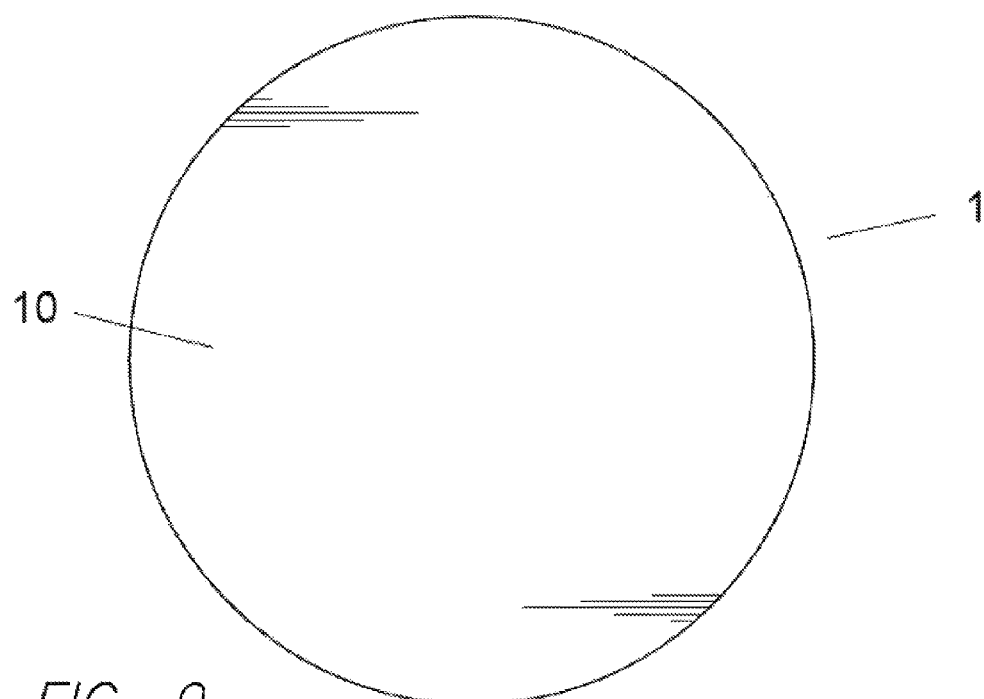
FIG. 9 is a top view of the device.
Figure 10:
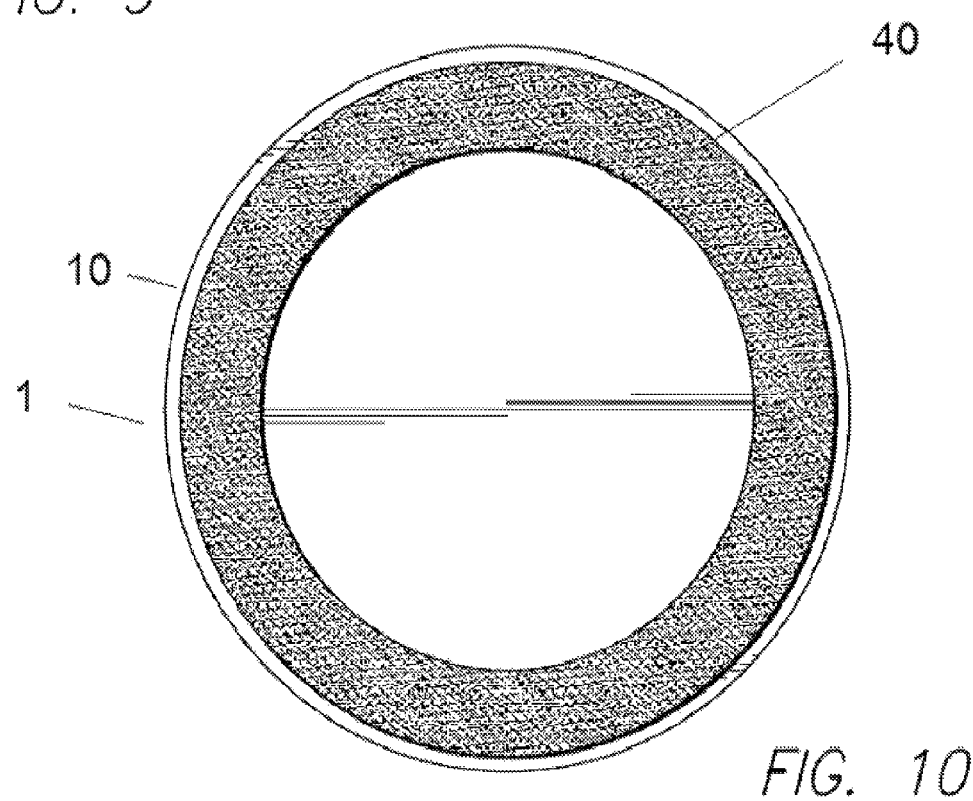
FIG. 10 is a bottom view of the device.

FIG. 7 displays a prospective side view of the device 1 in its ready pre-injection state while FIG. 8 shows a true side view. FIG. 9 displays a top view and FIG. 10 is a bottom view of the device 1.

As to a further discussion of the manner of usage and operation of the present invention, the same should be apparent from the above description. Accordingly, no further discussion relating to the manner of usage and operation will be provided.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur by those skilled in the art, it is not desired to limit the invention to the exact construction and operation shown and described, and accordingly, all suitable modifications and equivalents may be resorted to, falling within the scope of the invention.

I claim:

1. A process for the injection of a liquid comprising: providing a device having a chamber having a proximal end and a distal end, wherein the chamber is closed on the proximal end, open on the distal end, sealed by a moveable elastomeric seal, and contains a liquid to be injected, the device further comprising a base structure containing a plurality of needles and a compressible ring placed on the top of the chamber; applying pressure, causing the compressible ring to force the base structure into the chamber, forcing the needles to penetrate the compressible ring, forcing the moveable elastomeric seal into the chamber, and displacing the liquid through the needles.

2. A process according to claim 1, further comprising: injecting the liquid into skin.

3. A process according to claim 1, wherein the chamber is cylindrical in shape.

4. A process according to claim 1, wherein the chamber is collapsible.

5. A process according to claim 1, wherein the liquid is liquid anesthesia.

6. A process according to claim 1, wherein the liquid is liquid medicine.

7. A process according to claim 1, wherein the compressible ring is made of foam.

8. A process according to claim 1, wherein the chamber and the base structure have mating surfaces, and further comprising: rotating the mating surfaces before said liquid is displaced.

9. A process according to claim 1, wherein the compressible ring has a compressibility and wherein the needles have a length that is based on the compressibility of the compressible ring.

\* \* \* \* \*